US009358147B1

(12) United States Patent
Ancinec

(10) Patent No.: US 9,358,147 B1
(45) Date of Patent: Jun. 7, 2016

(54) ORTHOTIC JOINT STABILIZING ASSEMBLY

(71) Applicant: Craig Ancinec, Longview, TX (US)

(72) Inventor: Craig Ancinec, Longview, TX (US)

( * ) Notice: Subject to any disclaimer, the term of this patent is extended or adjusted under 35 U.S.C. 154(b) by 335 days.

(21) Appl. No.: 14/045,058

(22) Filed: Oct. 3, 2013

(51) Int. Cl.
*A61F 5/01* (2006.01)

(52) U.S. Cl.
CPC .................................. *A61F 5/0125* (2013.01)

(58) Field of Classification Search
CPC ................................................... A61F 5/0125
See application file for complete search history.

(56) References Cited

U.S. PATENT DOCUMENTS

| | | | |
|---|---|---|---|
| 4,433,679 A | 2/1984 | Mauldin et al. | |
| 4,865,024 A | 9/1989 | Hensley et al. | |
| 5,002,045 A | 3/1991 | Spademan | |
| 5,749,840 A * | 5/1998 | Mitchell | A61F 5/0123 602/23 |
| 7,048,704 B2 | 5/2006 | Sieller et al. | |
| 7,608,051 B1 | 10/2009 | Nace | |
| 7,963,933 B2 | 6/2011 | Nace | |
| 8,882,688 B1 * | 11/2014 | Ancinec | A61F 5/0125 128/882 |
| 2003/0153853 A1 | 8/2003 | Houser | |
| 2005/0192522 A1 | 9/2005 | Houser | |
| 2010/0056970 A1 * | 3/2010 | Nace | A61F 5/0123 602/26 |
| 2011/0098618 A1 | 4/2011 | Fleming | |
| 2011/0105969 A1 | 5/2011 | Nace | |
| 2013/0035623 A1 * | 2/2013 | Nace | A61F 5/0123 602/16 |
| 2013/0110020 A1 * | 5/2013 | Ingimundarson | A61F 5/0123 602/16 |

* cited by examiner

*Primary Examiner* — Nicholas Woodall
*Assistant Examiner* — Tarla Patel
(74) *Attorney, Agent, or Firm* — R. Keith Harrison

(57) ABSTRACT

An orthotic joint stabilizing assembly includes an assembly hinge; a first support and a second support carried by and pivotal with respect to each other about the assembly hinge; a hinge tension adjusting assembly including an eccentric tension adjusting cam carried by the assembly hinge, the tension adjusting cam adjustable between a plurality of tensioning positions; and a cam adjustment knob carried by the tension adjusting cam, the cam adjustment knob selectively engageable and disengageable with respect to the tension adjusting cam and operable to selectively lock the tension adjusting cam in a selected one of the plurality of tensioning positions. A hinge tensioning spring is carried by the first support and the second support and engages the tension adjusting cam of the hinge tension adjusting assembly. The hinge tensioning spring applies tension to the assembly hinge.

18 Claims, 5 Drawing Sheets

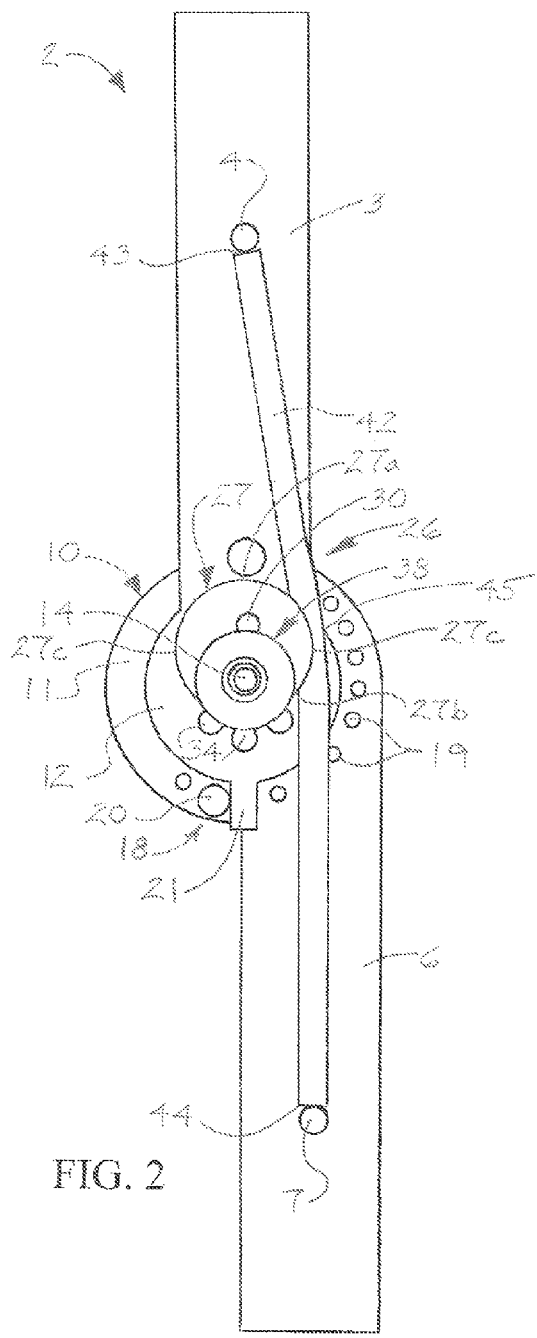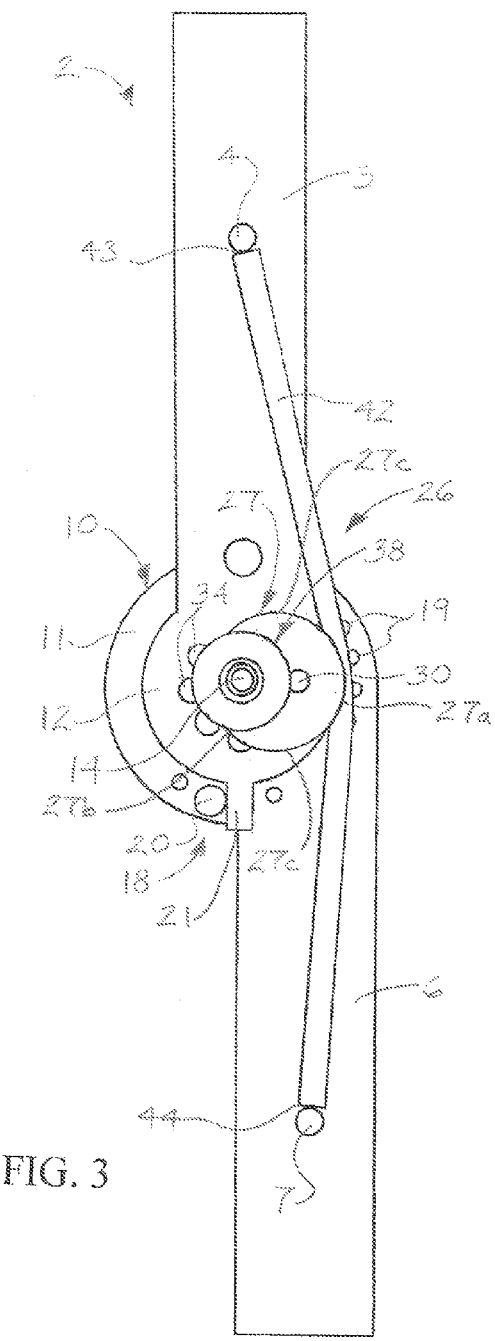
FIG. 2
FIG. 3

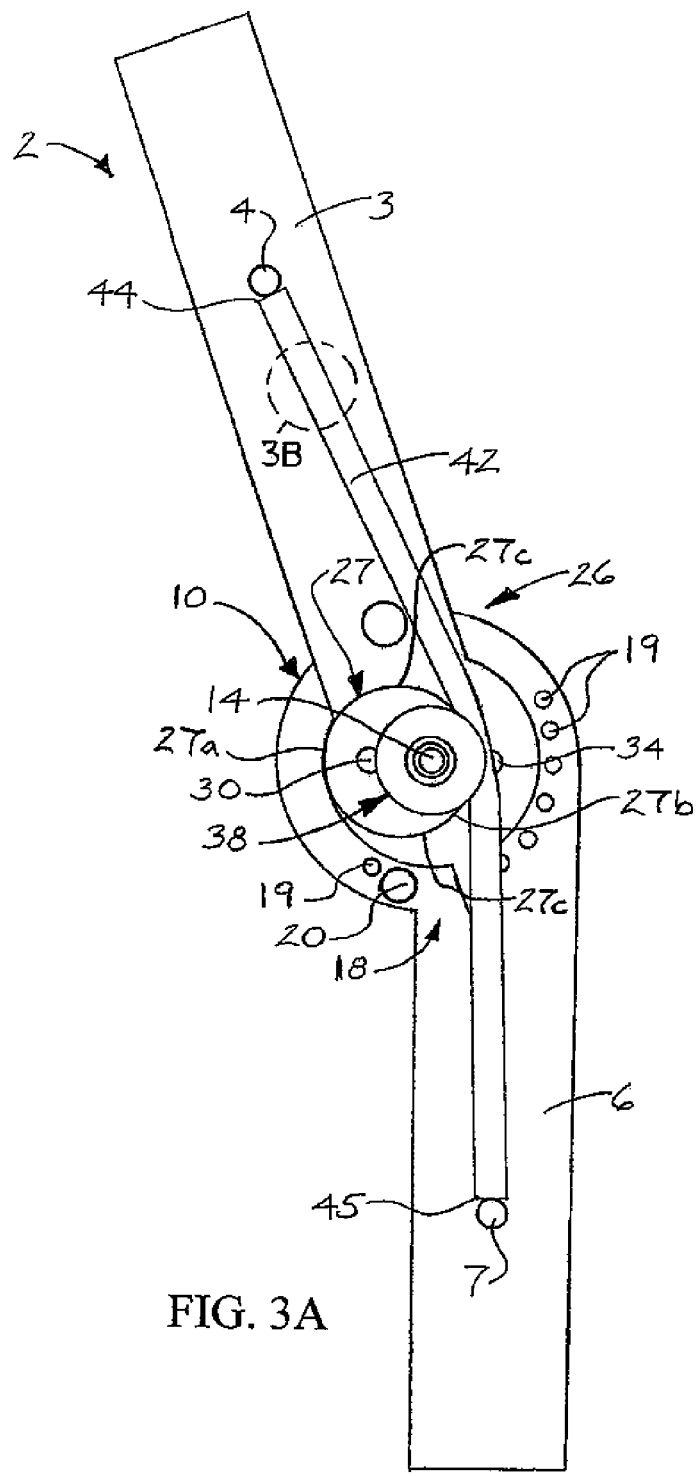
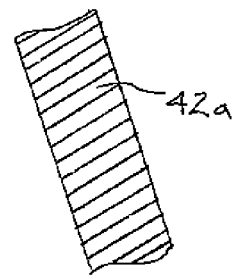
FIG. 3A
FIG. 3B

ORTHOTIC JOINT STABILIZING ASSEMBLY

CROSS-REFERENCE TO RELATED APPLICATIONS

This application is related to U.S. application Ser. No. 13/373,478, filed Nov. 15, 2011 and entitled "ORTHOTIC JOINT STABILIZING ASSEMBLY".

FIELD

Illustrative embodiments of the disclosure generally relate to orthotic devices. More particularly, illustrative embodiments of the disclosure relate to an orthotic joint stabilizing assembly which is particularly suitable for stabilizing a knee of a patient having compromised leg strength in a full extension position.

BACKGROUND

Some medical conditions can result in reduced control or strength of a person's limbs and compromise the function of limb joints. For example, stroke patients may have a compromised ability to straighten the legs at the knees due to reduced control or strength of the quadriceps muscles. This reduced ability to straighten the legs at the knees may be manifested, for example, when the person attempts to stand from a sitting position and the legs buckle at the knees.

Accordingly, an orthotic joint stabilizing assembly which is particularly suitable for stabilizing the knee of a patient having compromised leg control or strength in a full extension position is needed.

SUMMARY

Illustrative embodiments of the disclosure are generally directed to an orthotic joint stabilizing assembly. An illustrative embodiment of the orthotic joint stabilizing assembly includes an assembly hinge; a first support and a second support carried by and pivotal with respect to each other about the assembly hinge; a hinge tension adjusting assembly including an eccentric tension adjusting cam carried by the assembly hinge, the tension adjusting cam adjustable between a plurality of tensioning positions; and a cam adjustment knob carried by the tension adjusting cam, the cam adjustment knob selectively engageable and disengageable with respect to the tension adjusting cam and operable to selectively lock the tension adjusting cam in a selected one of the plurality of tensioning positions. A hinge tensioning spring is carried by the first support and the second support and engages the tension adjusting cam of the hinge tension adjusting assembly. The hinge tensioning spring applies tension to the assembly hinge.

BRIEF DESCRIPTION OF THE DRAWINGS

Illustrative embodiments of the disclosure will now be made, by way of example, with reference to the accompanying drawings, in which:

FIG. 2 is a side view of an exemplary stabilizing assembly unit, with a hinge tension adjusting assembly adjusted to an intermediate tensioning position;

FIG. 3 is a side view of an exemplary stabilizing assembly unit, with the hinge tension adjusting assembly adjusted to a maximum tensioning position;

FIG. 3A is a side view of an exemplary stabilizing assembly unit, with the stabilizing assembly unit disposed in a partially bended configuration and FIG. 3B is an enlarged sectional view taken along section line 3B in FIG. 3A;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. Relative terms such as "upper" and "lower" herein are used with reference to relative positions of various elements with respect to each other in exemplary application of the orthotic joint stabilizing assembly and are not intended to be used in a limiting sense.

Figure 1:
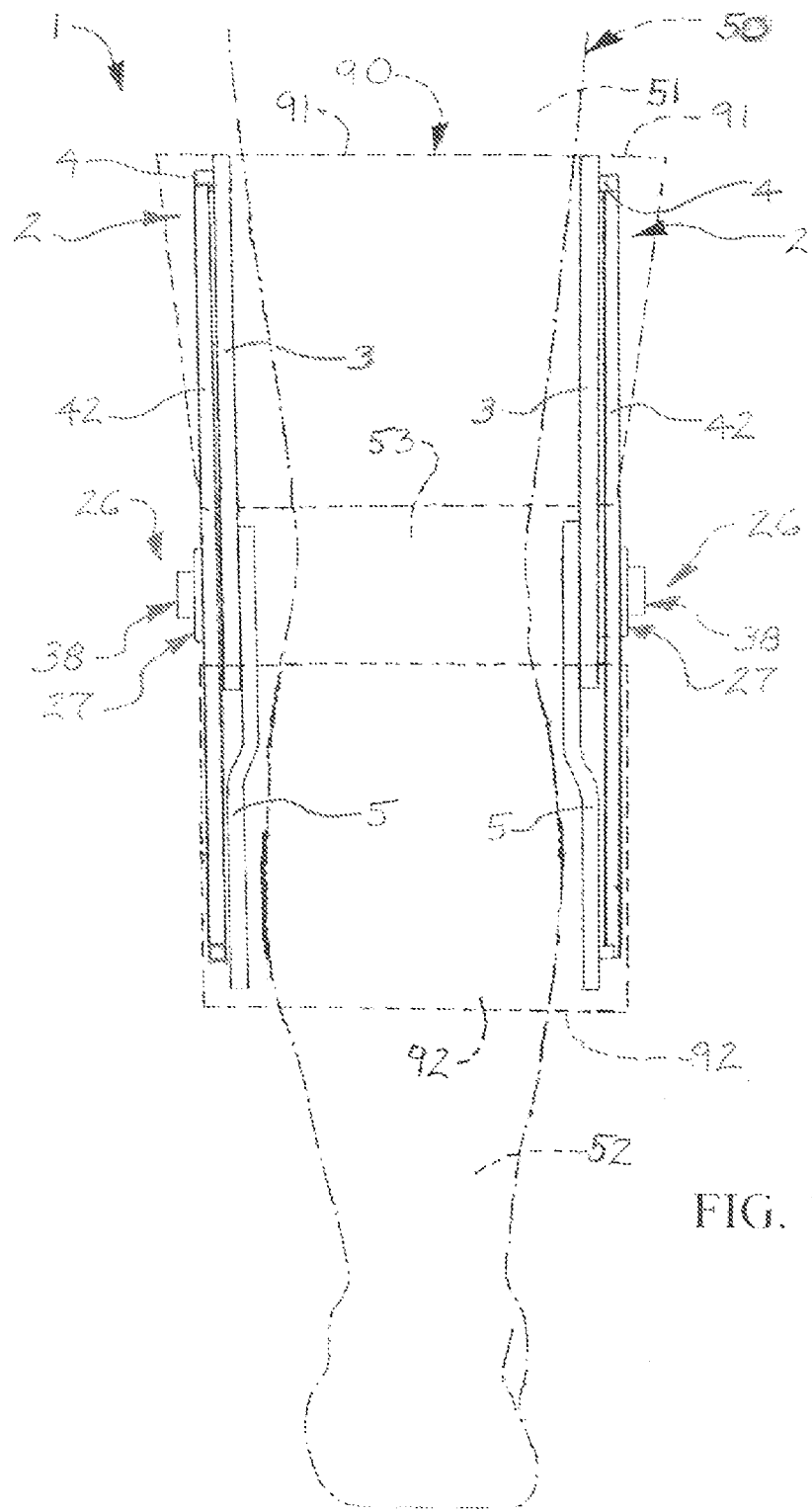
FIG. 1 is a front view of a pair of exemplary stabilizing assembly units of an illustrative embodiment of the orthotic joint stabilizing assembly, installed in a leg brace (illustrated in phantom) with the leg brace fitted on the leg (illustrated in phantom) of a patient to stabilize the knee of the patient in a full extension position in exemplary application of the orthotic joint stabilizing assembly.

Referring to the drawings, an illustrative embodiment of an orthotic joint stabilizing assembly, hereinafter assembly, is generally indicated by reference numeral 1. As illustrated in FIG. 1, the assembly 1 may include at least one stabilizing assembly unit 2 which in some applications may be installed in a leg brace 90 (illustrated in phantom) placed on the leg 50 of a user and extends adjacent to the user's knee 53 and may stabilize the user's knee 53 in a full extension position. In some applications, a pair of stabilizing assembly units 2 may be installed in the leg brace 90 on respective sides of the user's knee 53, as illustrated. The assembly 1 may be suitable for stabilizing the knee 53 of a user having a reduced or compromised ability to maintain the knee 53 in a full extension position due to any of a variety of medical ailments or conditions. In some applications, leg braces 90 may be placed on both legs 50 of the user with at least one assembly 1 installed in each leg brace 90 and may stabilize the knees 53 of both legs 50 in the full extension position.

Each stabilizing assembly unit 2 of the assembly 1 may include a generally elongated upper support 3 and a generally elongated lower support 6. An assembly hinge 10 may pivotally attach the lower support 6 to the upper support 3. An upper spring attachment tab 4 and a lower spring attachment tab 7 may be provided on the upper support 3 and the lower support 6, respectively, for purposes which will be hereinafter described. The upper support 3 and the lower support 6 may be steel, aluminum, composite fiber material and/or any other suitable material and may be fabricated using cutting, machining, stamping, casting, molding and/or other fabrication techniques according to the knowledge of those skilled in the art.

Figure 6:
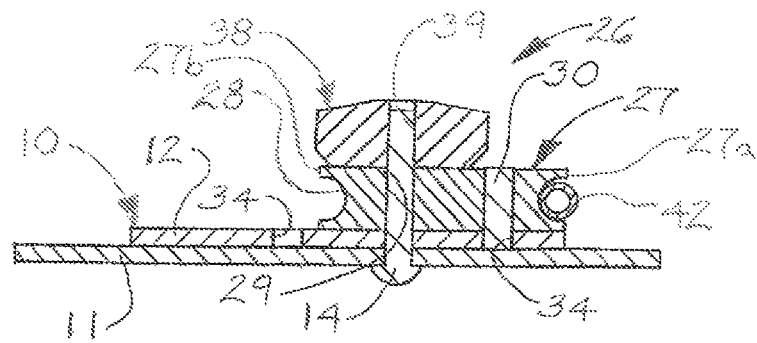
FIG. 6 is a cross-sectional view of an exemplary hinge tension adjusting assembly of an illustrative embodiment of the orthotic joint stabilizing assembly, taken along section lines 6-6 in FIG. 4, with the hinge tension adjusting assembly deployed in a fixed configuration.
Figure 7:
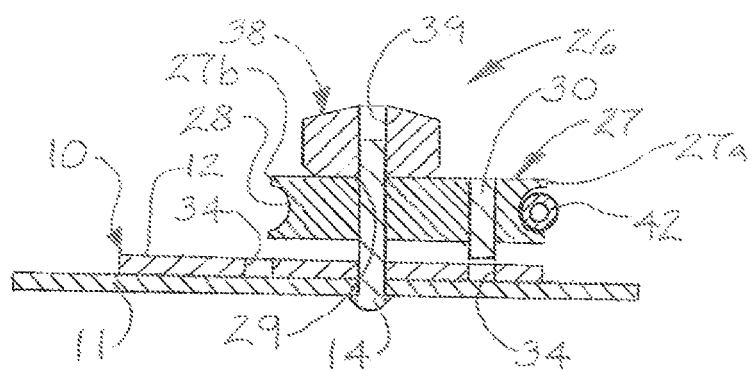
FIG. 7 is a cross-sectional view of an exemplary hinge tension adjusting assembly, taken along section lines 6-6 in FIG. 4, with the hinge tension adjusting assembly deployed in an adjusting configuration.

As illustrated in FIGS. 2-5, the assembly hinge 10 may include a base hinge plate 11 which terminates the upper support 3 and a cap hinge plate 12 which terminates the lower support 6. As illustrated in FIGS. 6 and 7, the cap hinge plate 12 may be disposed adjacent to the base hinge plate 11. A hinge pin 14 may extend through registering hinge pin openings (not illustrated) in the base hinge plate 11 and the cap hinge plate 12, respectively, to pivotally attach the cap hinge plate 12 to the base hinge plate 11. Accordingly, as illustrated in FIG. 3A, the upper support 3 and the lower support 6 may be capable of pivoting to any desired angle with respect to each other about the assembly hinge 10.

A hinge tension adjusting assembly 26 is provided on the assembly hinge 10. The hinge tension adjusting assembly 26 applies a selected magnitude of tension to the assembly hinge 10 for purposes which will be hereinafter described. As illustrated in FIGS. 6 and 7, the hinge tension adjusting assembly 26 may include a tension adjusting cam 27. The hinge pin 14 may eccentrically mount the tension adjusting cam 27 on the assembly hinge 10. A hinge pin opening 29 may extend through the tension adjusting cam 27 in offset relationship to the geometric center of the tension adjusting cam 27. Accordingly, the tension adjusting cam 27 may have a wide cam side 27a which is distal to the hinge pin 14, a narrow cam side 27b which is proximal to the hinge pin 14 and a pair of intermediate cam sides 27c which extend from the wide cam side 27a to the narrow cam side 27b. A circumferential spring groove 28 may be provided in the outer edge or surface of the tension adjusting cam 27. A cam adjustment pin 30 may extend from the tension adjusting cam 27 for insertion into a selected one of multiple cam adjustment openings 34 in the cap hinge plate 12 of the assembly hinge 10. As illustrated in FIGS. 2-5, the cam adjustment openings 34 may be arranged in a generally circular or semicircular pattern adjacent to the tension adjusting cam 27. Accordingly, the tension adjusting cam 27 can be set or locked at a selected tensioning position relative to the cap hinge plate 12, as illustrated in FIGS. 2-5, by rotating the tension adjusting cam 27 about the hinge pin 14 followed by insertion of the cam adjustment pin 30 into a selected one of the cam adjustment openings 34 for purposes which will be hereinafter described.

The hinge tension adjusting assembly 26 may further include a cam adjustment knob 38 which may threadably engage the hinge pin 14 and normally seats against the tension adjusting cam 27. As further illustrated in FIGS. 6 and 7, the cam adjustment knob 38 may include an internally-threaded hinge pin opening 39 which threadably receives and engages the hinge pin 14. As illustrated in FIG. 6, the cam adjustment knob 38 may normally be threaded on the hinge pin 14 against the tension adjusting cam 27 to bias the tension adjusting cam 27 against the cap hinge plate 12 and seat the cam adjustment pin 30 into the selected cam adjustment opening 34 in the cap hinge plate 12. As illustrated in FIG. 7, the cam adjustment knob 38 can be selectively unthreaded on the hinge pin 14 to disengage the tension adjusting cam 27 such that the cam adjustment pin 30 can be removed from the cam adjustment opening 34, the tension adjusting cam 27 rotated relative to the hinge pin 14 and the cam adjustment pin 30 inserted into another selected one of the cam adjustment openings 34. Thus, the cam adjustment pin 30 and the cam adjustment openings 34 may facilitate selective positioning of the tension adjusting cam 27 at minimum, intermediate and maximum tensioning positions, as will be hereinafter described. The tension adjusting cam 27, the cam adjustment pin 30 and the cam adjustment knob 38 of the hinge tension adjusting assembly 26 may be steel, aluminum, composite fiber material and/or any other suitable material and may be fabricated using cutting, machining, stamping, casting, molding and/or other fabrication techniques according to the knowledge of those skilled in the art.

As further illustrated in FIGS. 2-5, each stabilizing assembly unit 2 may include a hinge tensioning spring 42 which tensions the assembly hinge 10 and imparts resistance to pivoting of the upper support 3 and the lower support 6 relative to each other. Therefore, the hinge tensioning spring 42 may normally bias the upper support 3 and the lower support 6 in the straight position illustrated in FIG. 2. In some embodiments, the hinge tensioning spring 42 may include a generally elongated strip of flexible metal or, as illustrated in FIG. 3B, may be a coiled spring 42a, having an upper spring end 43 (FIG. 2) and a lower spring end 44. The upper spring end 43 of the hinge tensioning spring 42 may be attached to the upper spring attachment tab 4 on the upper support 3. The lower spring end 44 of the hinge tensioning spring 42 may be attached to the lower spring attachment tab 7 on the lower support 6. The hinge tensioning spring 42 engages the tension adjusting cam 27 of the hinge tension adjusting assembly 26. As illustrated in FIGS. 6 and 7, the hinge tensioning spring 42 may insert into the spring groove 28 in the outer edge or surface of the tension adjusting cam 27.

The hinge tensioning spring 42 imparts resistance to pivoting of the upper support 3 and the lower support 6 at the assembly hinge 10. When the upper support 3 and the lower support 6 are oriented in a straight configuration, as illustrated in FIG. 2, the tension adjusting cam 27 of the hinge tension adjusting assembly 26 may induce a spring bend 45 in the hinge tensioning spring 42 at the point of engagement, thereby breaking the initial resistance to bending or pivoting of the assembly hinge 10 which the hinge tensioning spring 42 would otherwise impart to the assembly hinge 10. Thus, the spring bend 45 may at least partially facilitate initial pivoting of the upper support 3 or the lower support 6 with respect to the assembly hinge 10 while imparting progressively increasing tension or resistance to pivoting as the angle between the upper support 3 and the lower support 6 decreases and the hinge tensioning spring 42 is stretched.

The hinge tension adjusting assembly 26 can be operated to selectively vary the magnitude of tension which the hinge tensioning spring 42 applies to the assembly hinge 10. Accordingly, the tension adjusting cam 27 can be selectively adjusted to the maximum tensioning position illustrated in FIG. 3 such that the hinge tensioning spring 42 engages the wide cam side 27a of the tension adjusting cam 27, which maximizes stretching or tensioning of the hinge tensioning spring 42 and thus, maximizes the magnitude of tension which the hinge tensioning spring 42 applies to the assembly hinge 10. Conversely, the tension adjusting cam 27 can be selectively adjusted to the minimum tensioning position illustrated in FIG. 4 such that the hinge tensioning spring 42 engages the narrow cam side 27b of the tension adjusting cam 27, which minimizes stretching or tensioning of the hinge tensioning spring 42 and thus, minimizes the magnitude of tension which the hinge tensioning spring 42 applies to the assembly hinge 10. As illustrated in FIG. 2, the tension adjusting cam 27 can be selectively adjusted to the intermediate tensioning position such that the hinge tensioning spring 42 engages one of the intermediate cam sides 27c of the tension adjusting cam 27, which stretches or tensions the hinge tensioning spring 42 to a magnitude which is between that of the minimum tensioning position (FIG. 4) and the maximum tensioning position (FIG. 3). Thus, the hinge tensioning spring 42 applies a magnitude of tension which is between that of the maximum tensioning position and the minimum tensioning position to the assembly hinge 10.

It will be appreciated by those skilled in the art that hinge tensioning springs 42 of various thicknesses and tension may be selectively interchangeable with each other on the upper support 3 and the lower support 6 depending on the desired resistance to bending or pivoting which is to be imparted to the assembly hinge 10. Generally, the thicker the hinge tensioning spring 42, the greater the initial resistance which must be overcome by the tension adjusting cam 27 to induce the spring bend 45 and facilitate pivoting of the upper support 3 and/or the lower support 6 at the assembly hinge 10. It will be recognized and understood that the hinge tensioning spring 42 which is illustrated in FIGS. 2-5 is exemplary only and that any spring design which is consistent with the purpose of resisting pivoting or bending of the upper support 3 and/or the lower support 6 with respect to the assembly hinge 10 may be used in implementation of the orthotic joint stabilizing assembly 1.

Figure 4:
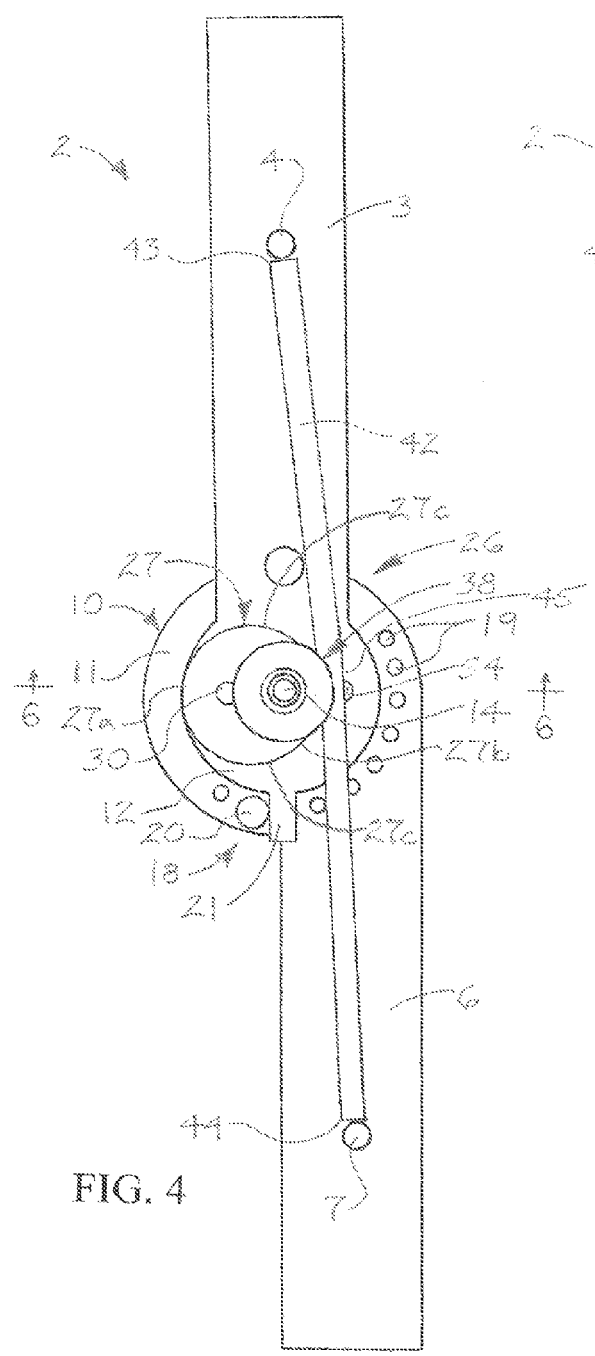
FIG. 4 is a side view an exemplary stabilizing assembly unit, with the hinge tension adjusting assembly adjusted to a minimum tensioning position.
Figure 5:
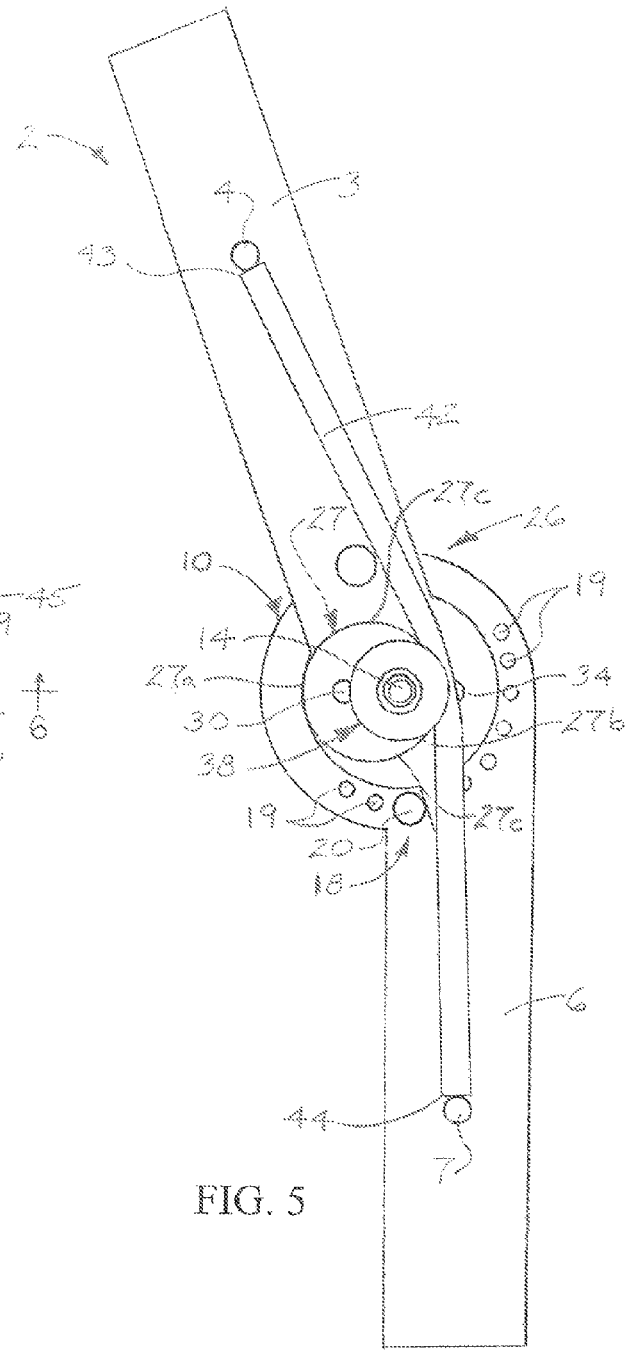
FIG. 5 is a side view of an exemplary stabilizing assembly unit, with a hinge angle adjusting assembly adjusted to a bended configuration.

As further illustrated in FIGS. 2-5, a hinge angle adjusting assembly 18 may be provided on the assembly hinge 10. The hinge angle adjusting assembly 18 may include multiple hinge angle adjusting openings 19 which extend through the base hinge plate 11. A hinge angle adjustment pin 20 engages a selected one of the hinge angle adjusting openings 19. A hinge angle abutment flange 21 may extend from the cap hinge plate 12. Upon biasing of the assembly hinge 10 via the hinge tensioning spring 42, the hinge angle abutment flange 21 may engage the hinge angle adjustment pin 20. Accordingly, as illustrated in FIGS. 4 and 5, the hinge angle adjustment pin 20 stops or retains the upper support 3 and the lower support 6 at a selected angle relative to each other depending on which of the hinge angle adjusting openings 19 the hinge angle adjustment pin 20 engages.

Referring again to FIG. 1 of the drawings, in exemplary application, a pair of assemblies 1 may be used in conjunction with each of a pair of leg braces 90 (one of which is illustrated in phantom) to stabilize both knees 53 (illustrated in front view) of a user in a full extension position. Stabilization of the user's knees 53 may be necessary to enable the user to stand without buckling of the user's knees 53. The user may have a reduced or compromised ability to maintain the user's knees 53 in a full extension position due to any of a variety of medical ailments or conditions. For example, stroke patients may have a compromised ability to maintain the knees 53 in a full extension position while standing.

The leg brace 90 may have a conventional design and may generally include an upper leg brace portion 91 which is fitted on the upper leg 51 and a lower leg brace portion 92 which is fitted on the lower leg 52. Exemplary leg braces 90 which are suitable for implementation of the assembly 1 are well-known in the art and include those manufactured by RCAI (Restorative Care of America) and the Donjoy Corp., for example and without limitation. The stabilizing assembly units 2 are positioned on opposite sides of the user's leg 50 with the assembly hinges 10 of the respective stabilizing assembly units 2 positioned adjacent to respective sides of the user's knee 53, as illustrated. Accordingly, the assembly 1 stabilizes the knee 53 of the user in a full extension position particularly as the user stands from a sitting position. The user may facilitate bending of the knee 53 by contracting the hamstring muscles in the user's leg 50, causing the upper support 3 and/or the lower support 6 to pivot with respect to the assembly hinge 10 against the bias imparted by the hinge tensioning spring 42. The tension adjusting cam 27 of the hinge tension adjusting assembly 26 may induce a spring bend 45 in the hinge tensioning spring 42, overcoming the initial resistance to bending which is normally imparted by the hinge tensioning spring 42 and facilitating bending of the assembly hinge 10 as was heretofore described with respect to FIGS. 2-5. The hinge tension adjusting assembly 26 can be operated to selectively apply the various magnitudes of tension to the hinge tensioning spring 42 by selective positioning of the tension adjusting cam 27, as was heretofore described with respect to FIGS. 2-5, depending on the needs of the patient.

While the preferred embodiments of the disclosure have been described above, it will be recognized and understood that various modifications can be made in the disclosure and the appended claims are intended to cover all such modifications which may fall within the spirit and scope of the disclosure.

What is claimed is:

1. An orthotic joint stabilizing assembly, comprising:
an assembly hinge;
a first support and a second support carried by and pivotal with respect to each other about the assembly hinge;
a hinge tension adjusting assembly including:
an eccentric tension adjusting cam carried by the assembly hinge, the eccentric tension adjusting cam adjustable between a plurality of tensioning positions, the eccentric tension adjusting cam comprises a wide cam side, a narrow cam side and a pair of intermediate cam sides; and
a cam adjustment knob carried by the eccentric tension adjusting cam, the cam adjustment knob selectively engageable and disengageable with respect to the eccentric tension adjusting cam and operable to selectively lock the eccentric tension adjusting cam in a selected one of the plurality of tensioning positions;
a hinge tensioning spring carried by the first support and the second support and engaging the eccentric tension adjusting cam of the hinge tension adjusting assembly, the hinge tensioning spring applying tension to the assembly hinge; and
wherein the eccentric tension adjusting cam can be adjusted to a maximum tensioning position such that the hinge tensioning spring engages the wide cam side of the tension adjusting cam to maximize tension the hinge tensioning spring applies to the assembly hinge and the eccentric tension adjusting cam can be adjusted to a minimum tensioning position such that the hinge tensioning spring engages the narrow cam side of the tension adjusting cam to minimize tension the hinge tensioning spring applies to the assembly hinge.

2. The orthotic joint stabilizing assembly of claim 1 wherein the assembly hinge comprises a base hinge plate and a cap hinge plate rotatable with respect to the base hinge plate, and the first support is carried by the base hinge plate and the second support is carried by the cap hinge plate.

3. The orthotic joint stabilizing assembly of claim 1 further comprising a spring groove in the eccentric tension adjusting cam, and wherein the hinge tensioning spring engages the spring groove.

4. The orthotic joint stabilizing assembly of claim 1 further comprising a plurality of cam adjustment openings in the assembly hinge and a cam adjustment pin carried by the eccentric tension adjusting cam, and wherein the cam adjustment pin is adapted to engage a selected one of the plurality of cam adjustment openings to selectively lock the eccentric tension adjusting cam in the selected one of the plurality of tensioning positions.

5. The orthotic joint stabilizing assembly of claim 1 wherein the hinge tensioning spring comprises a coiled spring.

6. The orthotic joint stabilizing assembly of claim 1 wherein the plurality of tensioning positions comprises the minimum tensioning position, the maximum tensioning position and an intermediate tensioning position.

7. The orthotic joint stabilizing assembly of claim 1 further comprising a first spring attachment tab carried by the first support and a second spring attachment tab carried by the second support, and wherein the hinge tensioning spring comprises a first spring end engaging the first spring attachment tab and a second spring end engaging the second spring attachment tab.

8. An orthotic joint stabilizing assembly, comprising:
an assembly hinge;
a first support and a second support carried by and pivotal with respect to each other about the assembly hinge;
a hinge pin extending through the assembly hinge;
a hinge tension adjusting assembly including:
an eccentric tension adjusting cam pivotally carried by the hinge pin of the assembly hinge, the hinge pin offset relative to a geometric center of the eccentric tension adjusting cam and the eccentric tension adjusting cam adjustable between a plurality of tensioning positions, the eccentric tension adjusting cam comprises a wide cam side, a narrow cam side and a pair of intermediate sides; and
a cam adjustment knob adjustably carried by the hinge pin, the cam adjustment knob selectively engageable and disengageable with respect to the eccentric tension adjusting cam and operable to selectively lock the eccentric tension adjusting cam in a selected one of the plurality of tensioning positions;
a hinge tensioning spring carried by the first support and the second support and engaging the eccentric tension adjusting cam of the hinge tension adjusting assembly, the hinge tensioning spring applying tension to the assembly hinge; and
wherein the eccentric tension adjusting cam can be adjusted to a maximum tensioning position such that the hinge tensioning spring engages the wide cam side of the tension adjusting cam to maximize tension the hinge tensioning spring applies to the assembly hinge and the eccentric tension adjusting cam can be adjusted to a minimum tensioning position such that the hinge tensioning spring engages the narrow cam side of the tension adjusting cam to minimize tension the hinge tensioning spring applies to the assembly hinge.

9. The orthotic joint stabilizing assembly of claim 8 wherein the assembly hinge comprises a base hinge plate and a cap hinge plate rotatable with respect to the base hinge plate, and the first support is carried by the base hinge plate and the second support is carried by the cap hinge plate.

10. The orthotic joint stabilizing assembly of claim 8 further comprising a spring groove in the eccentric tension adjusting cam, and wherein the hinge tensioning spring engages the spring groove.

11. The orthotic joint stabilizing assembly of claim 8 further comprising a plurality of cam adjustment openings in the assembly hinge and a cam adjustment pin carried by the eccentric tension adjusting cam, and wherein the cam adjustment pin is adapted to engage a selected one of the plurality of cam adjustment openings to selectively lock the eccentric tension adjusting cam in the selected one of the plurality of tensioning positions.

12. The orthotic joint stabilizing assembly of claim 8 wherein the hinge tensioning spring comprises a coiled spring.

13. The orthotic joint stabilizing assembly of claim 8 wherein the plurality of tensioning positions comprises the minimum tensioning position, the maximum tensioning position and an intermediate tensioning position.

14. The orthotic joint stabilizing assembly of claim 8 further comprising a first spring attachment tab carried by the first support and a second spring attachment tab carried by the second support, and wherein the hinge tensioning spring comprises a first spring end engaging the first spring attachment tab and a second spring end engaging the second spring attachment tab.

15. An orthotic joint stabilizing assembly, comprising:
an assembly hinge including:
a base hinge plate;
a cap hinge plate adjacent to the base hinge plate; and
a hinge pin pivotally attaching the cap hinge plate to the base hinge plate;
a first support carried by the base hinge plate;
a second support carried by the cap hinge plate;
a hinge tension adjusting assembly including:
a plurality of cam adjustment openings in the cap hinge plate of the assembly hinge, the plurality of cam adjustment openings arranged in a generally circular pattern;
an eccentric tension adjusting cam pivotally carried by the hinge pin of the assembly hinge adjacent to the cap hinge plate of the assembly hinge, the hinge pin offset relative to a geometric center of the eccentric tension adjusting cam and the eccentric tension adjusting cam adjustable between a plurality of tensioning positions, the eccentric tension adjusting cam comprises a wide cam side, a narrow cam side and a pair of intermediate sides;
a cam adjustment pin carried by the eccentric tension adjusting cam, the cam adjustment pin adapted to engage a selected one of the plurality of cam adjustment openings to selectively lock the eccentric tension adjusting cam in the selected one of the plurality of tensioning positions; and
a cam adjustment knob adjustably carried by and threadably engaging the hinge pin, the cam adjustment knob selectively engageable and disengageable with respect to the eccentric tension adjusting cam and operable to selectively lock the eccentric tension adjusting cam in a selected one of the plurality of tensioning positions by maintaining the cam adjustment pin in the selected one of the plurality of cam adjustment openings;
a hinge tensioning spring carried by the first support and the second support and engaging the eccentric tension adjusting cam of the hinge tension adjusting assembly, the hinge tensioning spring applying tension to the assembly hinge; and wherein the eccentric tension adjusting cam can be adjusted to a maximum tensioning position such that the hinge tensioning spring engages the wide cam side of the tension adjusting cam to maximize tension the hinge tensioning spring applies to the assembly hinge and the eccentric tension adjusting cam can be adjusted to a minimum tensioning position such that the hinge tensioning spring engages the narrow cam side of the tension adjusting cam to minimize tension the hinge tensioning spring applies to the assembly hinge.

16. The orthotic joint stabilizing assembly of claim 15 further comprising a spring groove in the eccentric tension adjusting cam, and wherein the hinge tensioning spring engages the spring groove.

17. The orthotic joint stabilizing assembly of claim 15 wherein the hinge tensioning spring comprises a coiled spring.

18. The orthotic joint stabilizing assembly of claim 15 wherein the eccentric tension adjusting cam comprises a pair of intermediate cam sides, and the plurality of tensioning positions comprises an intermediate tensioning position.

\* \* \* \* \*